(12) United States Patent
Müller

(10) Patent No.: US 6,607,697 B1
(45) Date of Patent: Aug. 19, 2003

(54) METHOD AND DEVICE FOR SUPPLYING READY-TO-USE DIALYSIS FLUID

(75) Inventor: Carsten Müller, Euerbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/232,521

(22) Filed: Jan. 19, 1999

(30) Foreign Application Priority Data

Jan. 19, 1998 (DE) .......................................... 198 01 768

(51) Int. Cl.$^7$ .......................... A61M 1/36; A61M 37/00; B01D 61/00; C02F 9/00; C02F 1/44
(52) U.S. Cl. ........................ 422/44; 604/5.01; 210/647; 210/739; 210/96.2; 210/257.2; 210/321.71; 210/929
(58) Field of Search .............................. 604/4–5, 28–31, 604/5.02–5.04, 6.09, 6.1, 6.11; 210/646–47, 650, 653, 739, 742, 746, 321.65, 321.71, 929, 96.1, 96.2, 257.1, 257.2, 321.6, 321.72, 348, 420; 422/44–48

(56) References Cited

U.S. PATENT DOCUMENTS

| | | | |
|---|---|---|---|
| 4,702,829 A | * | 10/1987 | Polaschegg et al. ..... 210/195.2 |
| 5,366,630 A | * | 11/1994 | Chevallet .................... 210/645 |
| 5,484,397 A | * | 1/1996 | Twardowski .................... 604/5 |
| 5,567,320 A | * | 10/1996 | Goux et al. .................. 210/739 |
| 5,744,031 A | * | 4/1998 | Bene ....................... 210/321.71 |
| 5,808,181 A | * | 9/1998 | Wamsiedler et al. | 
| 6,039,877 A | * | 3/2000 | Chevallet et al. |
| 6,042,784 A | * | 3/2000 | Wamsiedler et al. |
| 6,187,207 B1 | * | 2/2001 | Brauer |

FOREIGN PATENT DOCUMENTS

| | | |
|---|---|---|
| DE | 0444671 A | 6/1986 |
| EP | 0 265 795 A3 | 5/1988 |
| EP | 0 265 795 A2 | 5/1988 |
| EP | 692268 A | 1/1996 |
| EP | 0 694 312 A3 | 1/1996 |
| EP | 0 694 312 A2 | 1/1996 |

* cited by examiner

Primary Examiner—Angela D. Sykes
Assistant Examiner—Patricia Bianco
(74) Attorney, Agent, or Firm—Kenyon & Kenyon

(57) ABSTRACT

A method of supplying ready-to-use dialysis fluid in a machine for extracorporeal blood treatment, is described, said machine having, in addition to a dialyzer, at least one sterile filter divided by a microbe-retaining membrane into a first and second chamber. The temperature and/or conductivity of the dialysis fluid flowing through the sterile filter is monitored. To prevent dialysis fluid whose temperature and/or conductivity does not correspond to a preset temperature and/or conductivity value from flowing out of the second chamber of the sterile filter into the dialyzer after rinsing off the membrane of the sterile filter, the dialysis fluid flowing out of the sterile filter is first removed into the drain through a bypass line until the proper values are established. Only then is the dialyzer connected to the dialysis fluid path. In addition, the invention relates to a machine for extracorporeal blood treatment with a device for supplying ready-to-use dialysis fluid.

15 Claims, 3 Drawing Sheets

METHOD AND DEVICE FOR SUPPLYING READY-TO-USE DIALYSIS FLUID

FIELD OF THE INVENTION

The present invention relates to a method of supplying ready-to-use dialysis fluid in a machine for extracorporeal blood treatment, and it concerns a machine for extracorporeal blood treatment with a device for supplying ready-to-use dialysis fluid.

BACKGROUND OF THE INVENTION

Dialysis fluid is usually prepared online from fresh water and an electrolyte concentrate, the latter being inherently sterile and freshwater usually being free of microorganisms. However, there is no guarantee that dialysis fluid prepared in this way will be absolutely sterile. German Patent No. 3,641,843 describes a hemodialysis machine in which the dialysis fluid circuit has a sterile filter upstream from the dialysis fluid chamber to supply an absolutely sterile dialysis fluid to the dialyzer.

In hemodiafiltration, dialysis fluid can be prepared online from fresh water and an electrolyte concentrate, and the replacement fluid can be prepared online from the dialysis fluid. Although the electrolyte concentrate is usually sterile, and fresh water does not usually contain any microorganisms, this does not guarantee that the dialysis fluid prepared online will be absolutely sterile and pyrogen-free, which is why dialysis fluid for preparing the replacement fluid is converted to an absolutely sterile and pyrogen-free condition. This is done by preparing dialysis fluid upstream from the dialyzer and passing it through at least one filter which is divided into two chambers by a hydrophilic membrane that retains microorganisms. Such a device with two sterile filters arranged in the dialysis fluid system is known from German Patent No. 3,444,671 A and European Patent No. 692,268 A, for example.

To prevent microbes or pyrogens from clogging the sterile filters, it is known that the membrane of the sterile filter may occasionally be rinsed off with dialysis fluid.

European Patent No. 694,312 A describes a hemodiafiltration machine with a sterile filter arranged in the dialysis fluid path, where its membrane can be rinsed off with dialysis fluid through a line. A bypass line connects the dialysis fluid inlet line leading to the dialyzer to the dialysis fluid outlet line leading to the drain.

With the known blood treatment equipment with sterile filters in the dialysis fluid path, there is the risk that dialysis fluid at the wrong temperature or conductivity might reach the dialyzer.

Although the first chamber of the sterile filter is flushed with dialysis fluid, for example, fluid dwells in the second chamber of the filter when the treatment is interrupted. Then after the treatment is continued, the fully cooled fluid is sent to the dialyzer. Dialysis fluid at an excessively high temperature can reach the dialyzer when there is a disturbance in the temperature control of the device for supplying dialysis fluid.

OBJECT OF THE INVENTION

The object of the present invention is to provide a method of supplying ready-to-use dialysis fluid in a machine for extracorporeal blood treatment, which increases the safety of the blood treatment inasmuch as dialysis fluid reaches the dialyzer at a predetermined temperature or conductivity even after passing through the sterile filter. This object is achieved according to the present invention as described and claimed herein.

Another object of the present invention is to create a machine for the extracorporeal blood treatment so that its safety is increased inasmuch as dialysis fluid reaches the dialyzer at a predetermined temperature or conductivity even after passing through the sterile filter. This object is achieved according to the present invention as described and claimed herein.

With the method and device according to the present invention, the second bypass valve is opened after the first bypass valve is closed, thus interrupting the rinsing operation in the first chamber of the sterile filter, so that fluid present in the second chamber of the filter at a temperature and/or conductivity not conforming to a preset level is discharged through the second bypass line into the outlet. This prevents dialysis fluid at the wrong temperature and/or with the wrong composition from reaching the dialyzer.

The temperature and/or conductivity of the dialysis fluid is monitored while the dialysis fluid is flowing to the outlet, bypassing the dialyzer. If the deviation in the measured conductivity and/or temperature from a predetermined conductivity and/or temperature value is below a certain limit value, the second bypass line is interrupted again. Then dialysis fluid at the correct temperature and/or conductivity reaches the dialyzer.

When the second bypass valve is opened, the flow path through the first chamber of the dialyzer is advantageously interrupted. The flow path is interrupted with a shutoff device arranged upstream from the dialyzer in the dialysis fluid inlet line. A second shutoff device is preferably provided downstream from the dialyzer in the dialysis fluid outlet line.

The conductivity and/or temperature of the dialysis fluid can be determined with a first measurement device arranged downstream of the sterile filter in the direction of flow away from the dialyzer or a second measurement device arranged in the dialysis fluid outlet line downstream from the second bypass line when the dialysis fluid flows through the second bypass line to the drain.

To ensure that only dialysis fluid with a certain conductivity and/or temperature will reach the dialyzer, the temperature and/or conductivity of the dialysis fluid is advantageously monitored with a measurement device arranged in the dialysis fluid inlet line upstream from the sterile filter. If the deviation in the measured temperature and/or conductivity from a preset temperature and/or conductivity value exceeds a certain limit, the first chamber of the sterile filter is switched to continuous flow through the first bypass line, and the part of the dialysis fluid path leading to the dialyzer is interrupted. The conductivity and/or temperature of the dialysis fluid is then advantageously monitored with the measurement device arranged in the dialysis fluid inlet line upstream from the sterile filter or with a measurement device advantageously arranged in the dialysis fluid outlet line downstream from the first bypass line. If the deviation in the temperature and/or conductivity from a preset temperature and/or conductivity value falls outside a certain limit, the bypass line is interrupted so that dialysis fluid again flows through the sterile filter. This ensures that only dialysis fluid at a certain conductivity and/or temperature will reach the dialyzer.

Maintaining accurate temperature and/or conductivity values in the dialysis fluid is also important in particular when substituate obtained online from the dialysis fluid is supplied to the patient.

Several embodiments of a machine for extracorporeal blood treatment with a device for supplying ready-to-use dialysis fluid are explained in greater detail below with reference to the drawings.

DETAILED DESCRIPTION OF THE PREFERRED EMBODIMENTS

Figure 1A:
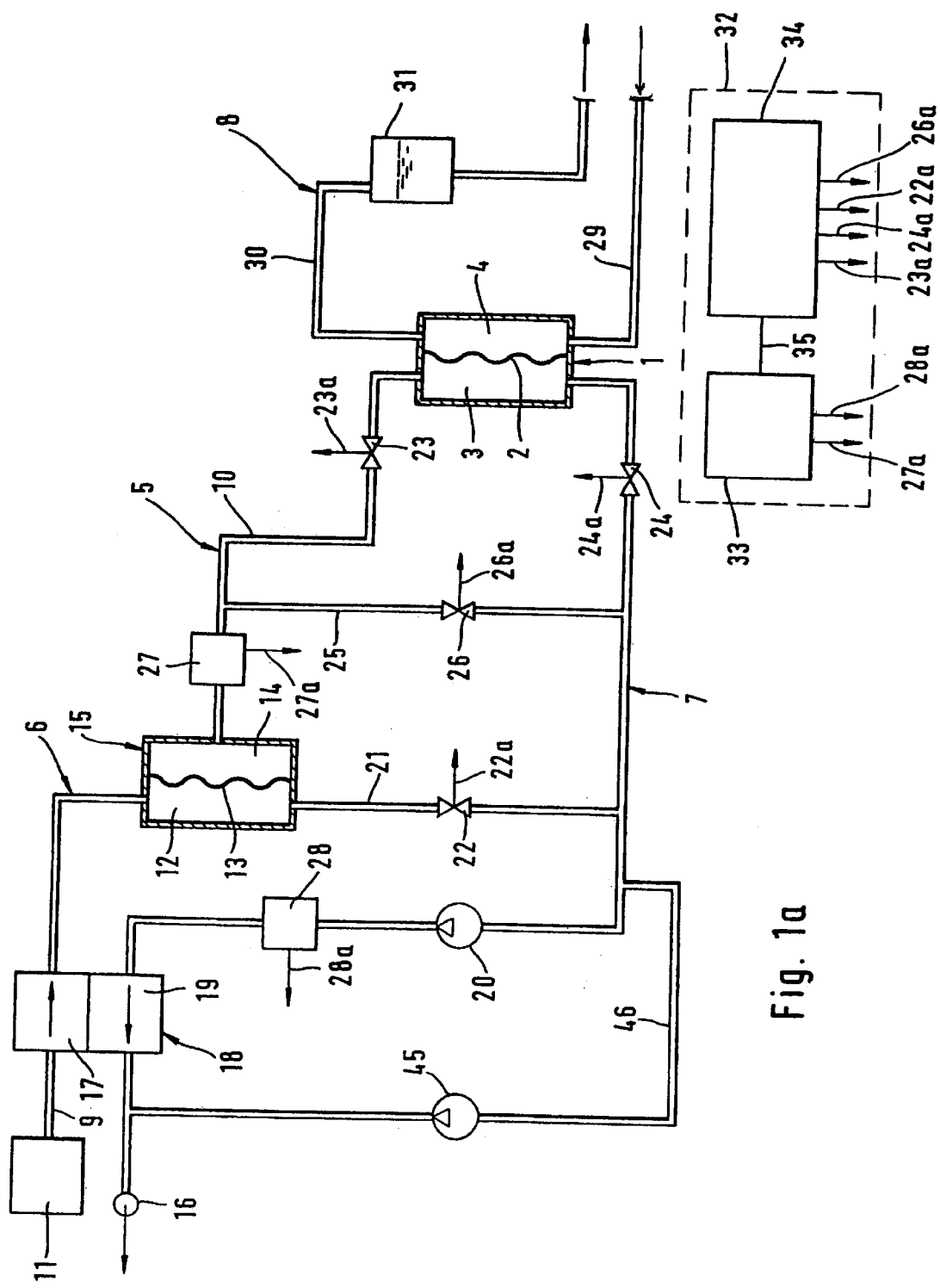
FIG. 1a: a schematic diagram of a hemodialysis machine with a device for supplying ready-to-use dialysis fluid.

FIG. 1 shows a schematic diagram of the essential components of a hemodialysis machine. The dialysis machine has a dialyzer 1 divided by a semipermeable membrane 2 into a first chamber 3 through which dialysis fluid flows and a second chamber 4 through which blood flows. The first chamber 3 is connected to a dialysis fluid path 5 having a dialysis fluid inlet line 6 and a dialysis fluid outlet line 7, while the second chamber 4 is connected to a blood path 8. Dialysis fluid inlet line 6 of dialysis fluid path 5 has a first line section 9 and a second line section 10. The first line section 9 connects a device 11 for supplying dialysis fluid to the inlet of a first chamber 12 of a sterile filter 15 which is subdivided by a microbe-retaining membrane 13 into first chamber 12 and second chamber 14. The second incoming line section 10 connects the outlet of the second chamber 14 of sterile filter 15 to the inlet of the first chamber 3 of dialyzer 1. The outlet of the first chamber 3 of dialyzer 1 is connected to an outlet 16 over dialysis fluid outlet line 7.

The first balancing chamber 17 of a balancing device 18 is connected to the first line section 9 of dialysis fluid inlet line 6, while the second chamber 19 of the balancing device is connected to dialysis fluid outlet line 7. Upstream from the second chamber 19 of balancing device 18, a dialysis fluid pump 20 is connected to dialysis fluid outlet line 7. A first bypass line 21, connected to a first bypass valve 22, leads from the outlet of the first chamber 12 of sterile filter 15 to dialysis fluid outlet line 7 upstream from dialysis fluid pump 20.

Upstream from dialyzer 1, a first shutoff device 23 is arranged in the second line section 10 of dialysis fluid inlet line 6, and downstream from the dialyzer, a second shutoff device 24 is arranged in dialysis fluid outlet line 7. A second bypass line 25 connected to a second bypass valve 26 connects the second line section 10 of dialysis fluid inlet line 6 upstream from the first shutoff device 23 to the dialysis fluid outlet line.7 downstream of the second shutoff device 24. A first device 27 for measuring the temperature and/or conductivity of the dialysis fluid is connected to the second line section 10 of the dialysis fluid inlet line 6, while a second device 28 for measuring the temperature and/or conductivity of the dialysis fluid is connected to dialysis fluid outlet line 7 downstream from the first bypass line 21.

Blood path 8 has a blood inlet line 29 coming from the patient and connected to the inlet of the second chamber 4 of dialyzer 1. The outlet of the second chamber 4 of the dialyzer leads to the patient through a blood outlet line 30 connected to drip chamber 31.

In addition, the hemodialysis machine has an ultrafiltration line 46 connected to an ultrafiltration pump 45. Ultrafiltration line 46 branches off from dialysis fluid outlet line 7 upstream from dialysis fluid pump 20 and opens into the dialysis fluid outlet line downstream from the second chamber 19 of the balancing device 18.

Device 32 for supplying ready-to-use dialysis fluid has an analyzer device 33 and a controlling device 34. Analyzer device 33 receives measured values from the first measurement device 27 over a data line 27a and receives measured values from the second measurement device 28 over a data line 28a. Controlling device 34 is connected to analyzer device 33 by a data line 35 and controls the first and second shutoff devices 23, 24 via control lines 23a, 24a and controls the first and second bypass valves 22, 26 via control lines 22a, 26a.

During the dialysis treatment, the first and second shutoff devices 23, 24 are opened and the first and second bypass valves 22, 26 are closed, so that dialysis fluid can flow from device 11 for supplying dialysis fluid through the first chamber 17 of balancing device 18 and sterile filter 15 into the first chamber 3 of the dialyzer. The dialysis fluid then flows out of the first chamber of the dialyzer to outlet 16 through the second chamber 19 of the balancing device 18.

The temperature and/or conductivity of the dialysis fluid is monitored continuously during the dialysis treatment with the first measurement device 27. The measured values from the first measurement device 27 are compared in the analyzer unit 33 with a preset temperature and/or conductivity value. If the deviation is greater than a certain limit value, controlling device 34 opens the first bypass valve 22 and closes the first and second shutoff devices 23, 24. In principle, however, it is sufficient if only one shutoff device is provided upstream from the dialyzer. Dialysis fluid then flows through the first bypass line 21 directly to outlet 16, with dialyzer 1 being separated from the dialysis fluid path. The temperature and/or conductivity is then monitored with the second measurement device 28. The measured values of the second measurement device 28 are compared with preset temperature and/or conductivity values in analyzer device 33. If the deviation is below a certain limit value, controlling device 34 closes the first bypass valve 22 again. Then the first and second shutoff devices 23, 24 can be opened again so that dialysis fluid again flows through dialyzer 1.

However, to prevent dialysis fluid whose temperature and/or conductivity does not conform to a preset temperature and/or conductivity from flowing out of the second chamber 14 of sterile filter 15 into dialyzer 1 after closing the first bypass valve 22, the dialyzer is not immediately connected to the dialysis fluid path again. After closing the first bypass valve 22, controlling device 34 first opens the second bypass valve 26, with the first and second shutoff devices 23, 24 remaining closed. Dialysis fluid in the second chamber 14 of sterile filter 15 can then flow out through the second bypass line 25 to outlet 16, bypassing dialyzer 1. The temperature and/or conductivity of the dialysis fluid is monitored either with the first or second measuring device 27, 28. Only when the deviation in temperature and/or conductivity from a preset temperature and/or conductivity value drops below a certain limit does controlling device 34 close the second bypass valve 26 and open the first and second shutoff devices 23, 24. As a result, only dialysis fluid whose temperature and/or conductivity corresponds to a preset temperature and/or conductivity value can reach the dialyzer.

Removing the dialysis fluid in the second chamber 14 of sterile filter 15 through the second bypass line 25 is especially advantageous when the first chamber of the sterile filter has previously been rinsed out with dialysis fluid to prevent clogging of the membrane with microbes or pyrogens. This prevents dialysis fluid that has already cooled during the rinsing operation in the second chamber of the sterile filter from reaching the dialyzer.

Figure 1B:
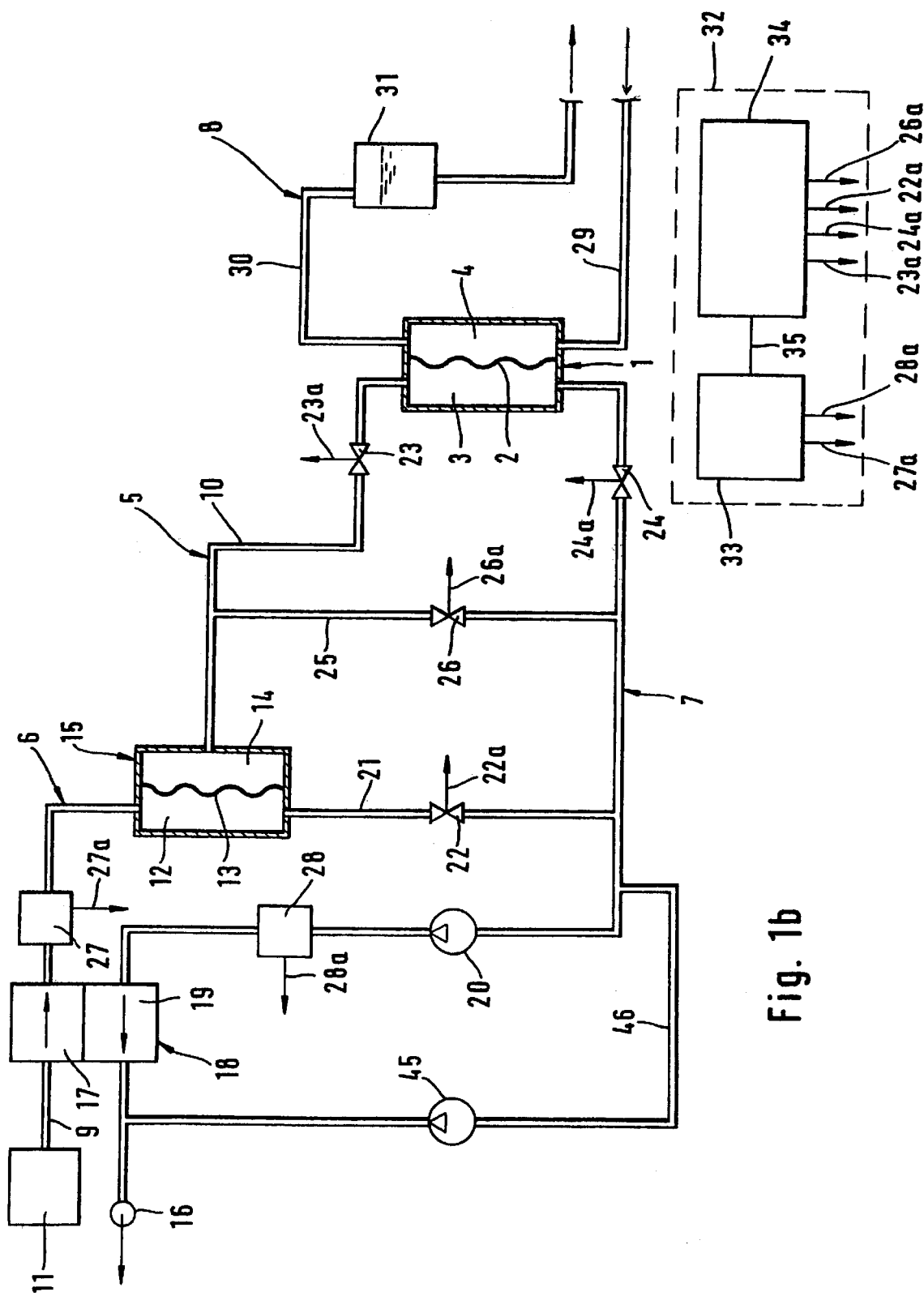
FIG. 1b: a schematic diagram of a second embodiment of a hemodialysis machine with a device for supplying ready-to-use dialysis fluid.

FIG. 1b shows another embodiment of the hemodialysis machine, which differs from the embodiment described with respect to FIG. 1 in that the first measurement device 27 is not located downstream from sterile filter 15 in the second line section 10 of dialysis fluid inlet line 6, but instead it is arranged upstream from sterile filter 15 in the first line section 9 of dialysis fluid inlet line 6. The parts of the hemodialysis machine according to FIG. 1b corresponding to the parts of the hemodialysis machine according to FIG. 1a are labeled with the same reference numbers. In this embodiment, the temperature and/or conductivity of the dialysis fluid flowing through the first bypass line 21 is monitored either with the first or second measurement device 27, 28. However, the temperature and/or conductivity of the dialysis fluid flowing through the second bypass line 25 in this embodiment can be monitored only with the second measurement device 28. Otherwise, the hemodialysis machine according to FIG. 1b operates according to the same program sequence as the machine according to FIG. 1a, so that no further explanation is necessary.

Figure 2:
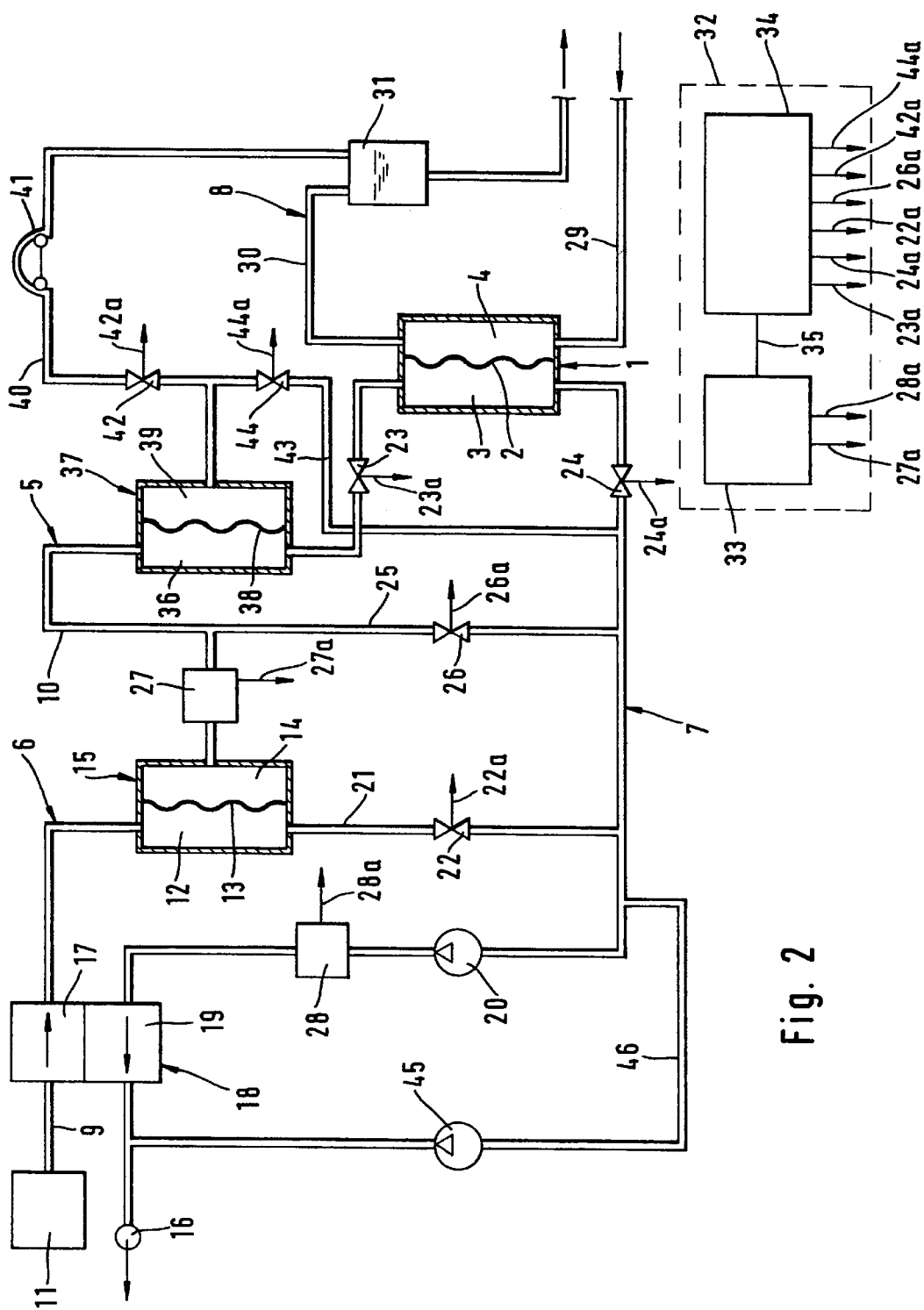
FIG. 2: a schematic diagram of a hemodiafiltration machine with a device for supplying ready-to-use dialysis fluid.

FIG. 2 shows a schematic diagram of a hemodiafiltration machine. The hemodiafiltration machine differs from the hemodialysis machine described with reference to FIGS. 1a and 1b in that a first chamber 36 of a second sterile filter 37 is connected upstream from the first shutoff devices 23 in the second line section 10 of dialysis fluid inlet line 6, said sterile filter being divided into a first chamber 36 and a second chamber 39 by a membrane 38 which retains microorganisms. The second sterile filter 37 is a substituate filter for obtaining substituate from the dialysis fluid during the hemodiafiltration treatment. The second chamber 39 of the substituate filter 37 is connected to drip chamber 31 by a substituate line 40. A substituate pump 41 is connected to the substituate line.

Upstream from substituate pump 41 a third shutoff device 42 is arranged in substituate line 40. Upstream from the third shutoff device 42, a third bypass line 43 branches off from, substituate line 40, opening into dialysis fluid outlet line 7 downstream from the second shutoff device 24. A third bypass valve 44 is connected to the third bypass line 43. The third shutoff device 42 and the third bypass valve 44 are driven by controlling device 34 via additional control lines 42a, 44a.

During the blood treatment, fluid can be removed from the patient through ultrafiltration line 46 by means of ultrafiltration pump 45. Fluid taken from the patient by pump 45 is added back at the same time through substituate line 40 by means of substituate pump 41, with the substituate fluid being obtained from the dialysis fluid online.

The temperature and/or conductivity of the dialysis fluid is monitored in the hemodiafiltration machine according to the same program as that used with the hemodialysis machine according to FIGS. 1a and 1b. No further explanation is necessary in this regard.

The hemodiafiltration machine has the advantage not only that dialysis fluid at the proper temperature and/or conductivity always reaches the dialyzer, but also that the substituate obtained from the dialysis fluid is always at the proper temperature. The first bypass line 21 prevents dialysis fluid at the wrong temperature and/or conductivity from reaching the dialyzer and prevents substituate at the wrong tempera-
ture from reaching the patient. In addition, the first bypass line serves to rinse out the dialyzer. The second bypass line makes it possible to set the parameters again quickly at the correct levels after an interruption, e.g., after rinsing off.

To check the substituate branch, controlling device 34 closes the third shutoff device 42 and opens the third bypass valve 44, so that substituate can flow out of the second chamber 39 of substituate filter 37 to outlet 16. As soon as the correct values, which are monitored with the second measurement device 28, have been established, controlling device 34 again closes the third bypass valve 44 and opens the third shutoff device 42, so that substituate can be supplied to the patient again with substituate pump 41.

What is claimed is:

1. A method of supplying ready-to-use dialysis fluid in extracorporeal blood treatment, comprising the steps of:
   (a) providing blood to be treated to an extracorporeal blood treatment machine having:
      a dialyzer divided by a semipermeable membrane into a dialysis fluid chamber connected to a dialysis fluid path and having a dialysis fluid chamber inlet and a dialysis fluid chamber outlet and a blood chamber connected to a blood path, the dialysis fluid path having a dialysis fluid inlet line and a dialysis fluid outlet line;
      a fluid filter provided in the dialysis fluid path, the fluid filter divided by a microbe-retaining membrane into a first filter chamber and a second filter chamber, the first filter chamber having an inlet and each filter chamber having an outlet;
      a first bypass line, having a first bypass valve and providing fluid connection between the first filter chamber outlet and the dialysis fluid outlet line;
      a second bypass line, having a second bypass valve and providing fluid connection between the dialysis fluid inlet line and the dialysis fluid outlet line;
      a measuring device provided in the dialysis fluid outlet line downstream of the first bypass line, the measuring device capable of measuring a dialysis fluid parameter selected from the group consisting of temperature and conductivity, and of generating a signal in response to the measured parameter; and
      a comparing device connected to the measuring device arranged and composed for receiving a signal from the measuring device and calculating the difference between the measured dialysis fluid parameter and a predetermined value for the parameter;
   (b) providing fresh dialysis fluid with the first bypass valve open, such that fluid flows through the first filter chamber into the first bypass line;
   (c) closing the first bypass valve and opening the second bypass valve such that fluid flows through the microbe retaining membrane into the second filter chamber, out the second filter chamber outlet through the second bypass line into the dialysis fluid outlet line and through the measuring device;
   (d) measuring the dialysis fluid parameter;
   (e) comparing the measured value for the parameter and a predetermined value for the parameter; and
   (f) closing the second bypass valve when the calculated difference is outside a pre-set limit value, such that dialysis fluid flows to the dialysis fluid chamber.

2. The method of claim 1, wherein opening the second bypass valve interrupts fluid flow to the dialysis fluid chamber.

3. The method of claim 1, wherein the extracorporeal blood treatment device further comprises a second measuring device adapted to measure a dialysis fluid parameter selected from the group consisting of temperature and conductivity, the second measuring device further adapted to generate a signal, the second measuring device provided in the dialysis fluid inlet line upstream of the second bypass line; and wherein the comparing device is connected to the second measuring device;

wherein step (d) of the method further comprises the steps of measuring the dialysis fluid parameter with the second measuring device and generating a signal; and wherein step (e) of the method further comprises the steps of calculating the difference between the second measured value and the predetermined value.

4. The method of claim 1, wherein the extracorporeal blood treatment device further comprises a second measuring device adapted to measure a dialysis fluid parameter selected from the group consisting of temperature and conductivity, the second measuring device further adapted to generate a signal, the second measuring device provided in the dialysis fluid path upstream of the fluid filter; and wherein the comparing device is connected to the second measuring device;

wherein step (d) of the method further comprises the steps of measuring the dialysis fluid parameter with the second measuring device and generating a signal; and wherein step (e) of the method further comprises the steps of calculating the difference between the second measured value and the predetermined value.

5. The method of claim 1, wherein the dialysis fluid inlet line further comprises:

a shutoff valve downstream of the second bypass line, the shutoff valve connected to the control device; wherein:

step (c) of the method further comprises closing the shutoff valve; and step (f) of the method further comprises opening the inlet line valve.

6. A method of supplying ready-to-use dialysis fluid in extracorporeal blood treatment, comprising the steps of:

(a) providing blood to be treated to an extracorporeal blood treatment machine having:

a dialyzer divided by a semipermeable membrane into a dialysis fluid chamber connected to a dialysis fluid path and having a dialysis fluid chamber inlet and a dialysis fluid chamber outlet and a blood chamber connected to a blood path, the dialysis fluid path having a dialysis fluid inlet line and a dialysis fluid outlet line;

a fluid filter provided in the dialysis fluid path, the fluid filter divided by a microbe-retaining membrane into a first filter chamber and a second filter chamber, the first filter chamber having an inlet and each filter chamber having an outlet;

a first bypass line, having a first bypass valve and providing fluid connection between the first filter chamber outlet and the dialysis fluid outlet line;

a second bypass line, having a second bypass valve and providing fluid connection between the dialysis fluid inlet line and the dialysis fluid outlet line;

a measuring device provided in the dialysis fluid outlet line downstream of the first bypass line, the measuring device capable of measuring a dialysis fluid parameter selected from the group consisting of temperature and conductivity, and of generating a signal in response to the measured parameter; and a comparing device connected to the measuring device arranged and composed for receiving a signal from the measuring device and calculating the difference between the measured dialysis fluid parameter and a predetermined value for the parameter;

(b) providing fresh dialysis fluid to the dialysis fluid path with the first and second bypass valves closed such that fluid flows through the fluid filter and the dialysis inlet line into the dialysis fluid chamber, through the dialysis fluid outlet line and the measuring device and into the drain;

(c) taking a first measurement of the dialysis fluid parameter;

(d) opening the first bypass valve in response to a calculated difference exceeding a pre-set value, thereby diverting dialysis fluid through the first bypass line into the dialysis fluid outline line;

(e) taking a second measurement of the dialysis fluid parameter;

(f) closing the first bypass valve in response to a calculated value falling below the pre-set value, thereby interrupting flow through the first bypass line; and (g) opening the second bypass valve, thereby allowing fluid flow through the second bypass line into the dialysis fluid outline line.

7. The method of claim 6, wherein the method further comprises the steps of:

(h) taking a third measurement of the dialysis fluid parameter; and (i) closing the second bypass valve in response to a calculated value falling below the pre-set value.

8. A device for extracorporeal blood treatment comprising:

a dialyzer divider by a semipermeable membrane into a dialysis fluid chamber connected to a dialysis fluid path and having,a dialysis fluid chamber inlet and a dialysis fluid chamber outlet and a blood chamber connected to a blood path, the dialysis fluid path having a dialysis fluid inlet line and a dialysis fluid outlet line;

a fluid filter provided in the dialysis fluid path, the fluid filter divided by a microbe-retaining membrane into a first filter chamber and a second filter chamber, the first filter chamber having an inlet and each filter chamber having an outlet;

a first bypass line, having a first bypass valve and providing fluid connection between the first filter chamber outlet and the dialysis fluid outlet line;

a second bypass line, having a second bypass valve and providing fluid connection between the dialysis fluid inlet line and the dialysis fluid outlet line, the second bypass line being in fluid communication with the second filter chamber of the fluid filter;

a measuring device provided in the dialysis fluid outlet line downstream of the first bypass line, the measuring device capable of measuring a dialysis fluid parameter selected from the group consisting of temperature and conductivity, and of generating a signal in response to the measured parameter; and a comparing device connected to the measuring device arranged and composed for receiving a signal from the measuring device and calculating the difference between the measured dialysis fluid parameter and a predetermined value for the parameter;

wherein closing the first bypass valve and opening the second bypass valve diverts dialysis fluid through the second bypass line into the dialysis fluid outlet line and closing the second bypass valve allows dialysis fluid flow to the dialysis fluid chamber; and wherein a control device opens the second bypass valve when the first bypass valve is closed and closes the second bypass valve when the calculated difference falls below a pre-set limit value.

9. The device of claim 8, wherein the device further comprises an inlet shutoff valve provided in the dialysis fluid inlet line, the inlet shutoff valve being connected to the control device;

wherein the control device closes the inlet shutoff valve when the second bypass valve is opened and opens the inlet shutoff valve when the second bypass valve is closed.

10. The device of claim 9, wherein the device further comprises an outlet shutoff valve provided in the dialysis fluid outlet line, the outlet shutoff valve being connected to the control device;

wherein the control device closes the outlet shutoff valve when the second bypass valve is opened and opens the outlet shutoff valve when the second bypass valve is closed.

11. The device of claim 10, wherein the control device opens the first bypass valve when the calculated difference in the pre-set limit value.

12. The device of claim 11, wherein the control device closes the first bypass valve, opens the second bypass valve and closes the inlet and outlet shutoff valves when the calculated difference falls below the pre-set limit value.

13. The device of claim 12, wherein the control device closes the second bypass valve and opens the inlet and outlet shutoff valves when the calculated value falls below the preset limit value.

14. The device of claim 8, wherein the device further comprises a second measuring device provided in the dialysis fluid inlet line upstream of the second bypass line and connected to the comparing device, the second measuring device adapted for measuring a dialysis fluid parameter selected from the group consisting of temperature and conductivity.

15. The device of claim 8, wherein the device further comprises a second measuring device provided in the dialysis fluid path upstream of the fluid filter and connected to the comparing device, the second measuring device adapted for measuring a dialysis fluid parameter selected from the group consisting of temperature and conductivity.

* * * * *